United States Patent
Ritter et al.

(10) Patent No.: US 11,255,779 B2
(45) Date of Patent: Feb. 22, 2022

(54) PROCESS FOR QUANTITATIVE DETERMINATION OF FATTY ACID ESTERS IN FUELS

(71) Applicant: QUANTARED TECHNOLOGIES GMBH, Vienna (AT)

(72) Inventors: Wolfgang Ritter, Vienna (AT); Bernhard Lendl, Vienna (AT)

(73) Assignee: Quantared Technologies GmbH, Vienna (AT)

( * ) Notice: Subject to any disclaimer, the term of this patent is extended or adjusted under 35 U.S.C. 154(b) by 0 days.

(21) Appl. No.: 16/644,626

(22) PCT Filed: Jul. 25, 2018

(86) PCT No.: PCT/EP2018/070229
§ 371 (c)(1),
(2) Date: Mar. 5, 2020

(87) PCT Pub. No.: WO2019/048124
PCT Pub. Date: Mar. 14, 2019

(65) Prior Publication Data
US 2021/0080388 A1 Mar. 18, 2021

(30) Foreign Application Priority Data
Sep. 6, 2017 (EP) .................................. 17189615

(51) Int. Cl.
*G01N 21/3577* (2014.01)
*G01N 21/75* (2006.01)
(Continued)

(52) U.S. Cl.
CPC ......... *G01N 21/3577* (2013.01); *G01N 21/75* (2013.01); *G01N 33/22* (2013.01); *G01N 2021/3595* (2013.01)

(58) Field of Classification Search
CPC ............. G01N 21/88; G01N 2201/061; G01N 15/147; G01N 2021/3595; G01N 21/3577
See application file for complete search history.

(56) References Cited

U.S. PATENT DOCUMENTS

2012/0261567 A1* 10/2012 Voorhees ............ H01J 49/0418
250/282
2021/0239610 A1* 8/2021 Christensson ..... G01N 21/3577

FOREIGN PATENT DOCUMENTS

GB       2466802 A  *  7/2010  ......... G01N 21/3577
WO  WO-2016026891 A1 *  2/2016  ................ C10L 1/02

OTHER PUBLICATIONS

Alcaraz et al., "EC-QCL mid-IR transmission spectroscopy for monitoring dynamic changes of protein secondary structure in aqueous solution on the example of β-aggregation in alcohol-desaturated α-chymotrypsin,"; Anal Bioanal Chem (2016) 408:3933-3941.

(Continued)

*Primary Examiner* — David P Porta
*Assistant Examiner* — Fani Boosalis
(74) *Attorney, Agent, or Firm* — Singleton Law, PLLC; Chainey P. Singleton

(57) ABSTRACT

The present invention provides a method for the quantitative determination of contaminants in the form of fatty acid esters in jet fuels, wherein the analyte is the fatty acid ester fatty acid methyl ester (FAME) and/or the fatty acid ester fatty acid ethyl ester (FAEE), wherein the analyte undergoes a chemical reaction which is selective for it and which influences the intensity for the carbonyl band of the respective ester group with the formation of a modified analyte and the variation in the concentration of analyte in the sample, which is the jet fuel together with FAME and/or FAEE, is measured using the reduction in the intensity of the carbonyl band and/or the increase in the concentration of the modified (Continued)

analyte is measured using the increase in the intensity of a band which is characteristic for the modification.

12 Claims, 2 Drawing Sheets

(51) Int. Cl.
*G01N 33/22* (2006.01)
*G01N 21/35* (2014.01)

(56) References Cited

OTHER PUBLICATIONS

European Search Report in EP 17 18 9615 dated Feb. 2, 2018, pp. 1-8.
Hemighaus et al., "Alternative Jet Fuels"; Addendum 1 to Aviation Fuels Technical Review (FTR-3/A1); 2006; pp. 1-16.
Knothe; "Monitoring a Progressing Transesterification Reaction by Fiber-Optic Near Infrared Spectroscopy with Correlation to 1H Nuclear Magnetic Resonance Spectroscopy," JAOCS, vol. 77, No. 5, (2000); pp. 489-493.
Tariq et al.,; "Activity of homogeneous and heterogeneous catalysts, spectroscopic and chromatographic characterization of biodiesel: A review,"; Renewable and Sustainable Energy Reviews 16 (2012) pp. 6303-6316.

\* cited by examiner

PROCESS FOR QUANTITATIVE DETERMINATION OF FATTY ACID ESTERS IN FUELS

CROSS-REFERENCE TO RELATED APPLICATIONS

This application is a National Stage of International Application No. PCT/EP2018/070229, filed Jul. 25, 2018 which claims priority to and the benefit of Application No. EP 17189615.2, filed Sep. 6, 2017. The contents of each of which is incorporated by reference in their entirety.

TECHNICAL FIELD OF THE INVENTION

The present invention relates to a method for the quantitative determination of contaminants in the form of analytes based on esters, in particular fatty acid esters such as, for example, fatty acid methyl esters or fatty acid ethyl esters (FAME/FAEE), or glycerides in jet fuel.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Rapid and accurate routine measurements of contaminants, additives or components of liquid fuels count among the principal tasks in industrial measurement engineering. The specifications for the production of fuels are strict, but during transport in pipelines, tankers, storage tanks or filters, they may become contaminated. In addition, the addition of additives at various points along the supply chain is permitted.

The ester of a fatty acid with methanol as the alcohol is termed a fatty acid methyl ester (FAME); correspondingly, the ester of a fatty acid with ethanol as the alcohol is termed a fatty acid ethyl ester (FAEE). Mixtures of FAMEs and FAEEs obtained from plant or animal fats (e.g. rapeseed oil) are used as fuels for diesel engines and are generally known as biodiesel. In many countries, mixing biodiesel into diesel fuel is already regulated by law. In addition to FAME and FAEE, traces of their starting products (glycerides) may be contained in the fuel.

FAME, FAEE and glycerides are solid or liquid at room temperature and some of their properties are very similar to those of diesel fuel, but at the same time they are solvents with effects that differ from that of diesel fuel, which can lead to technical problems with sealing materials in engine systems. Fatty acid methyl esters and fatty acid ethyl esters can therefore in principle only be used as an alternative fuel when the sealing materials in the engines used are resistant to FAME or FAEE.

In today's global supply systems, such as pipelines, tankers, trains and ships, frequently, a huge variety of fuels and fluids are transported one after the other, but protective measures are employed which are designed to minimize cross-contamination. FAME in particular, however, has the ability to adhere strongly to surfaces, whereupon small quantities of FAME could also be found in jet fuels. These contaminants usually arise because jet fuel is transported in the same transport system after propellants containing FAME and/or FAEE. In addition, FAME and FAEE from biodiesel can remain on the walls of multiproduct pipelines and therefore contaminate any jet fuel that follows.

Fame in jet fuel has been categorized by the Joint Inspection Group (JIG) as a hazardous substance. Studies have shown that there is a potential risk, even in low concentrations. This risk ranges from the corrosion of bearings, deposits in the propellant jets, compromises to sealing material, to major variations in the viscosity of the propellant at low temperatures. The international specifications Def. Stan. 91.-91 and ASTM D1655 currently prescribe a limit of <50 mg/kg of FAME in jet fuel. In larger quantities, refuelling of aircraft and starting the engines is prohibited, and if the engines are erroneously operated with jet fuel containing more than 50 mg/kg of FAME, compulsory additional maintenance work on the engines is required.

In order to determine the FAME/FAEE content in jet fuel, at the current point in time, essentially four methods are employed. These include three chromatographic methods, gas chromatography—mass spectroscopy (GC-MS), high performance liquid chromatography (HPLC) and Heart Cut gas chromatography; as well as one Fourier transform infrared spectrometric method (FTIR). For the quantitative determination of the concentration of FAME/FAEE/glycerides, at the moment, GC-MS is used the most. Although this method is accurate and specific, it can only be carried out in a certificated analytical laboratory and the analysis takes a long time. In addition, with chromatographic methods, short-chain FAME, for example coconut methyl ester, cannot be distinguished from other components of the jet fuel.

During the production of biodiesel, the process for the transesterification of plant fats and oils is monitored by following the reaction conversion using FTIR measurements. In "Renewable and Sustainable Energy Reviews", vol. 16, No. 8, Tariq et al. Described the production of biodiesel which was composed of fatty acid methyl esters, by transesterification of a variety of plant oils. In that regard, as an example, the proportion of fatty acids in the mixture of the reaction products was determined using FTIR spectroscopy. In the Journal of the American Oil Chemists' Society, Vol. 77, No. 5, Knothe describes monitoring the process for the transesterification of a plant oil to form fatty acid methyl ester during the production of biodiesel by means of IR spectroscopy. The use of IR spectroscopy which is based on a quantum cascade laser has been described by Alcaraz et al. in the Journal of Analytical and Bioanalytical Chemistry when monitoring dynamic variations in secondary structures of proteins in aqueous solutions.

SUMMARY OF THE INVENTION

There is therefore an urgent need for a simplified method for the analysis of FAME, ideally in order to carry out analyses on site or in a field laboratory.

In recent years, an FTIR analytical method has been developed in which the sample to be analysed (jet fuel+FAME) is fed through a disposable cartridge, which cartridge has been filled with a sorbent material (for example silica gel). By means of this sorbent material, FAME is retained by adsorption within the cartridge, whereupon the sample being passed through it is freed from FAME. By means of an FTIR measurement, the sample is compared in front of and behind the cartridge, in order to determine the FAME content. In this, above all, the bands for the carbonyl group at 1749 $cm^{-1}$ are evaluated. The disadvantage here is that the sorbent material usually does not have a sufficient selectivity for FAME, so that other (polar) substances are adsorbed. Thus, in this analysis method, an additional chemometric model (PLS) is necessary in order to subtract the influence of these impurities.

Thus, the objective of the present invention is to provide a measurement method for esters, in particular fatty acid esters (FAME/FAEE, but also glycerides) in jet fuels, wherein the measurement method does not suffer from the disadvantages of the prior art. In this regard, in a method for the quantitative determination of contaminants in the form of fatty acid esters such as fatty acid methyl esters or fatty acid ethyl esters and/or glycerides in jet fuels, the analyte (for example FAME/FAEE/glycerides) undergoes a chemical reaction which is selective for it and which influences the intensity of the carbonyl band for the respective ester group with the formation of a modified analyte and the variation in the concentration of analyte in the sample is measured using the reduction in the intensity of the carbonyl band, and/or the increase in the concentration of the modified analyte is measured using the increase in the intensity of a band that is characteristic of the modification. Because of the higher selectivity of the selective chemical reaction compared with the adsorption of the analyte employed in the prior art, a higher selectivity for the measurement method can be obtained. By means of the comparison with the original, unreacted sample (containing the analytes) as a specific background, matrix effects can also be corrected. Substantially fewer impurities undergo this selective chemical reaction and, in this manner, the method is more robust and less susceptible to interference. The threshold for detection can be reduced; the higher selectivity of the "sample preparation" means that with individual wavelength points in the spectrum, a robust evaluation can be obtained. In this manner, in a preferred embodiment of the method in accordance with the invention, a highly spectrally tuneable FTIR can be replaced by light sources such as, for example, quantum cascade lasers (QCL), with a limited spectral tunability. The advantages of the method in accordance with the invention are:

higher selectivity
great robustness as regards impurities in different jet fuels
improved sensitivity
miniaturization because of QCL
reduced production costs.

In accordance with a preferred embodiment of the present invention, the measurement of the variation in concentration of analyte is carried out by IR spectroscopy.

This is advantageous when the measurement of the variation in the concentration of analyte is carried out using FTIR spectroscopy.

It has also been shown to be advantageous when the measurement of the variation in the concentration of analyte is carried out using IR spectroscopy employing a quantum cascade laser. In particular, using QCL means that it is possible to evaluate the variation in the intensity of a band in analytes or modified analytes in a small spectral window.

Jet fuel is not a pure substance, but a blend of paraffins, naphthenes and aromatics in various ratios. The addition of additives means that, depending on the composition, the blend is guaranteed to comply with the required specifications. This means that jet fuel from different refineries, pipelines or even batches from the same source can differ widely from a spectral viewpoint. Thus, as is generally the case with optical measurement methods, it is not possible to measure small concentrations of components in jet fuel without generating a sample-specific background.

In the method in accordance with the invention, the sample (jet fuel+FAME/FAEE/glyceride) undergoes a selective reaction during the course of the measurement; thus, for example, in accordance with a preferred embodiment of the present invention, FAME/FAEE/glyceride, or in general an ester or fatty acid ester to be determined, is transformed into the corresponding amide by adding an amine, wherein the variation in the concentration of FAME/FAEE/glyceride, or in general the variation in the concentration of the ester or fatty acid ester in the sample to be determined, can be measured with the aid of the reduction in the intensity of the carbonyl band for the ester and/or the increase in the intensity of the amide band for the amide which is formed.

Aminolysis of an ester

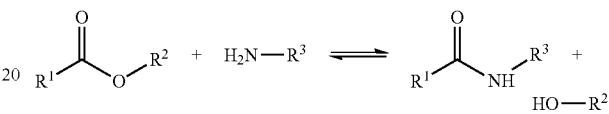

Aminolysis of a triglyceride

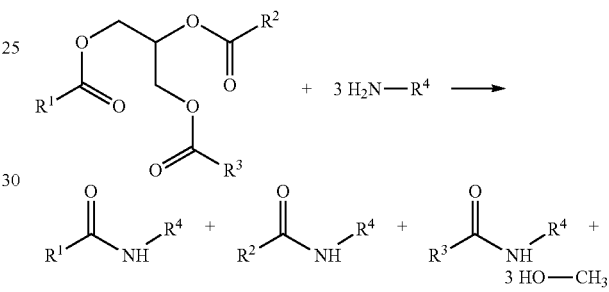

In accordance with a further preferred embodiment of the method in accordance with the invention, the ester or FAME/FAEE/glyceride is transformed into the corresponding other ester by adding another alcohol under suitable reaction conditions and the variation in the concentration of FAME/FAEE/glyceride, or in general the variation in the concentration of the ester or fatty acid ester to be determined, in the sample is measured with the aid of the reduction in the intensity of the carbonyl band for the ester and/or the increase in the intensity of the carbonyl band of the other ester. In this regard, the selective reaction is a transesterification of the fatty acid ester by adding another alcohol. The ester which is formed (i.e. the modified analyte) exhibits a displaced band for the carbonyl group which can be distinguished from the original band. Again, the reduction in the carbonyl band for the ester, FAME/FAEE or glyceride analyte and/or the increase in the carbonyl band of the modified analyte is evaluated. A slight disadvantage with this transesterification method may be that the measurement wavelength for the product bands may be spectrally close and therefore might have an influence on the measurement.

Transesterification using an alcohol

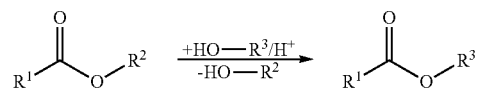

In both of the discussed reactions, the spectral properties of the sample vary, whereupon a determination of the analyte content is possible by means of comparative measurements. In this regard, both the reduction in the intensity of the carbonyl band for the analyte as well as the increase in the intensity of a specific band in the modified analyte may be used for the measurement method in accordance with the invention; by considering both variations and the relationship of the variations with respect to each other, the quantitative determination of the analyte is further facilitated.

The accompanying FIG. 1 shows the degradation of FAME (1) with the aid of the reduction in the carbonyl stretching frequency at 1749 $cm^{-1}$ and the spectrally sufficiently displaced increase in the corresponding amide as the reaction product (2) in the infrared absorption spectrum.

In accordance with a preferred embodiment of the present invention, the reaction for the formation of the modified analyte is enzymatically catalysed, particularly preferably in the presence of lipase. The use of other enzymes may also be considered, wherein these enzymes, or catalysts in general, should allow the reaction for modification of the analyte to proceed to completion as far as possible.

By means of the selective chemical reaction, the concentration of FAME/FAEE/glycerides in the sample is reduced, and in this case, in the case of FAME, in the infrared spectrum, this results in a reduction/displacement of the carbonyl band (1749 $cm^{-1}$), or in the case of aminolysis, to the appearance of an amide band (1690 $cm^{-1}$). The reduction in the original carbonyl band is measured and is transformed into the analyte concentration which is sought by means of a calibration. A further possible embodiment is the determination of the concentration of the analytes by measuring the increase in the intensity of the amide band.

The carbonyl group of the FAEE has its absorption maximum at 1742 $cm^{-1}$; in accordance with a preferred embodiment of the present invention, for example, the concentration of FAEE can be determined or calculated, by symmetrical evaluation at 1742 $cm^{-1}$, for example. The term "symmetrical evaluation" as used here in particular should be understood to mean an evaluation at ±2 $cm^{-1}$, in particular 5 $cm^{-1}$, particularly preferably ±10 $cm^{-1}$ about the cited absorption maximum; clearly, the determination of the concentration of analytes, however, may be carried out using other methods known to the person skilled in the art.

A possible unwanted side reaction when using aminolysis in the method in accordance with the invention is the transformation of FAME/FAEE/glyceride into other esters with the aid of alcohols. The absorption maximum for these esters is approximately 1742 $cm^{-1}$, which could interfere with a measurement at 1749 $cm^{-1}$. By means of the symmetrical evaluation at 1742 $cm^{-1}$ mentioned above, this effect can in fact be subtracted or minimized.

In accordance with a preferred embodiment of the method in accordance with the invention, for the purposes of quantitative determination, the method additionally uses the reaction kinetics/reaction kinetics for a qualitative determination. One advantage of this method is that by means of this qualitative determination, fatty acid esters from other analytes such as other ketones, for example, can be distinguished, and thus falsification of the quantitative determination of the contaminants in the form of fatty acid esters in jet fuels by other analytes is minimized.

In accordance with a preferred embodiment of the method in accordance with the invention, the method is used for the identification of or to exclude the identity of the contaminant. By means of the method in accordance with the invention, the exclusion method can determine what chemical compounds are in the contaminants in the jet fuel. In fact, the identity of the contaminant itself may not be determined with complete accuracy, however certain substances can be excluded. As an example, a very slow reaction in the method in accordance with the invention excludes the possibility that the contaminant in the jet fuel is FAEE/FAME/triglycerides.

BRIEF DESCRIPTION OF THE DRAWINGS

For a more complete understanding of the features and advantages of the present invention, reference is now made to the detailed description of the invention along with the accompanying figures.

DETAILED DESCRIPTION OF THE INVENTION

Figure 1:
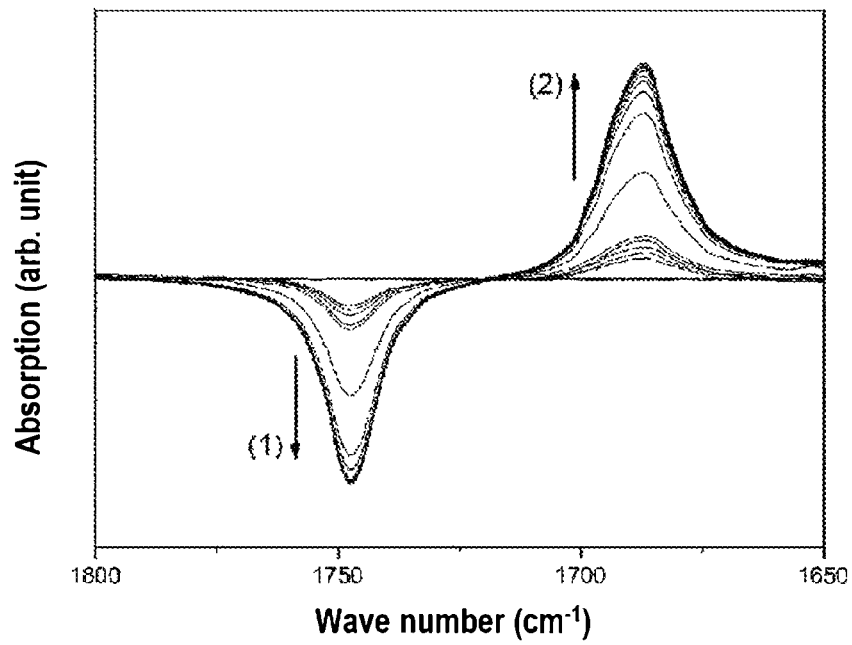
FIG. 1: shows the degradation of FAME (1) with the aid of the reduction of the carbonyl stretching frequency at 1749 $cm^{-1}$ and the sufficiently spectrally displaced increase in the corresponding amide as a reaction product (2) in the infrared absorption spectrum.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The present invention will now be explained in more detail with the aid of the cited examples, although the invention is not limited to the examples.

The following determinations were carried out:
FAME in jet fuel by means of aminolysis
FAEE in jet fuel by means of aminolysis
glyceryl trioleate in jet fuel by means of aminolysis
FAME in diesel by means of aminolysis
FAME in jet fuel by transesterification For the determination of FAME in jet fuel by means of aminolysis, additional measurements were carried out:
approved jet fuel additives
jet fuel screening.
General Method In a preferred embodiment, measuring instruments for carrying out the method consist of a flow cell, an infrared source (for example: Globar with or without spectral filter or QCL) together with a detector, pumps, valves, a system for dosing the reagents as well as a multi-way cartridge which contains the catalyst. The layer thickness of the flow cell is typically tailored to the illumination power of the infrared source used and to the IR transmission of the sample matrix.

At the start of a sequence of measurements, the measuring instrument is rinsed with the sample liquid to be analysed, and then a background is recorded with QCL or FTIR. After adding one of the reagents listed below, the sample liquid is pumped between flow cells and a cartridge containing the catalyst in a circuit. The analyte thereby undergoes a chemical reaction which is selective for it, which influences the intensity of the carbonyl bands for the relevant ester group, with the formation of a modified analyte and the variation in the concentration of analyte in the sample is measured using the reduction in the intensity of the carbonyl band and/or the increase in the concentration of the modified analyte being formed is measured using the increase in the intensity of a band which is characteristic for the modification. The kinetics of the reaction allow early threshold warnings to be determined, allow the entire course of the reaction to be monitored, and by measuring standard samples, allow the remaining activity of the catalyst in the reusable cartridge to be determined. After the reaction is complete, the measuring instrument is rinsed with sample liquid again in order to measure a second background. From the variation in the measured intensity between the background ($I_0$) and the reacted sample (I), the absorption (Abs) is determined using the Lambert-Beer law:

$$Abs = \log(I_0/I)$$

From this, and by comparison with calibration curves, the concentration of the analyte is given by:

concentration of analyte [mg/kg]=$(Abs*k+d)*\rho_C/\rho_S$ in which:
k=slope of calibration curve
d=axial intercept of calibration curve
$\rho_C$=density of calibration matrix, in kg/m$^3$
$\rho_S$ density of sample, in kg/m$^3$ As an example, for a measurement of jet fuel supplemented with 49.9 mg/kg of FAME, for a measured absorption of 17.81 mAU with the calibration curve k=2.79 mAU$^{-1}$ and d=−0.18 mg/kg, the calculated FAME concentration is 49.51 mg/kg. The density of the calibration matrix and of the sample were identical in this example.

Figure 2:
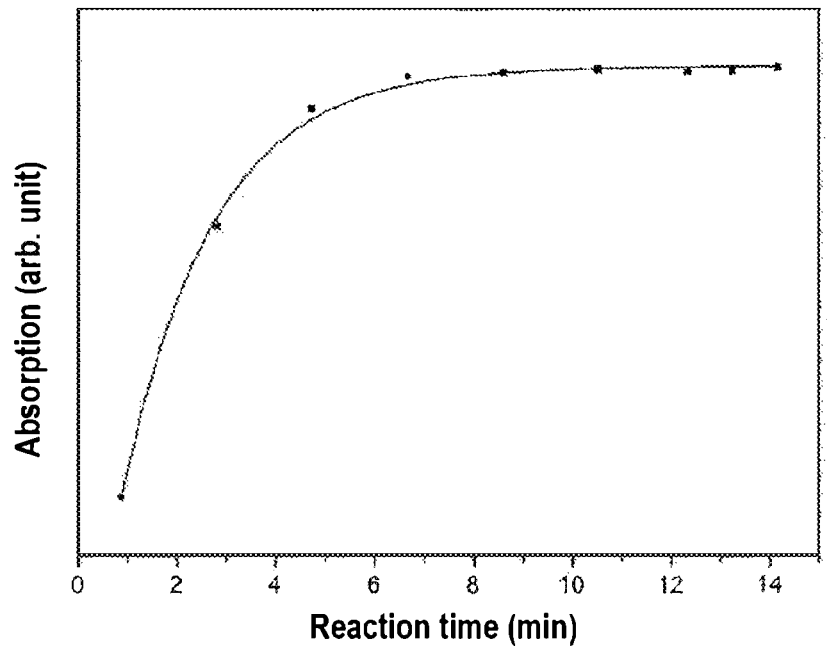
FIG. 2: shows the kinetics for the enzymatically catalysed reaction of FAME and amine to the corresponding amide (points) with an exponential fit (line) for the purposes of predicting the measurement.

FAME in Jet Fuel Using Aminolysis:

Aminolysis has been shown to be an advantageous variation, because under enzymatic catalytic conditions, it is complete in less than 20 minutes for FAME concentrations of less than 500 mg/kg (see accompanying FIG. 2).

TABLE 1

FAME in jet fuel using aminolysis

| Matrix | Analyte | Added concentration [mg/kg] | Calculated concentration [mg/kg] |
|---|---|---|---|
| Jet fuel | FAME mix from B7 | 0.0 | −0.02 |
| Jet fuel | FAME mix from B7 | 5.5 | 5.34 |
| Jet fuel | FAME mix from B7 | 11.1 | 11.26 |
| Jet fuel | FAME mix from B7 | 22.1 | 21.66 |
| Jet fuel | FAME mix from B7 | 199.3 | 200.19 |
| Jet fuel | FAME mix from B7 | 400.4 | 399.98 |

Table 1 shows examples of results for jet fuels which had been supplemented with a FAME mix (20% RME—Rape Methyl Ester, PME—Palm Methyl Ester, TME—Tallow Methyl Ester, SME—Soy Methyl Ester und UCOME—Used Cooking Oil Methyl Ester, as a seven percent solution in diesel; B7) in various concentrations.

The results show that 0-250 mg/kg FAME in jet fuel can be measured with an accuracy of <1 mg/kg. In order to determine FAME in jet fuel without the influence of FAEE and alcohols, all of the data were evaluated symmetrically around 1742 cm$^{-1}$.

The method in accordance with the invention was not only tested with the FAME mix cited above, which was tailored to the European market, but also with individual FAME types. The measurement results with a concentration around the permitted maximum of 50 mg/kg are listed in Table 2 below.

From Table 2, it can be seen that the accuracy for individual FAMEs was somewhat lower because FAME from different sources typically have different chain lengths. With short chain methyl esters such as CME (Coconut Methyl Ester, used in particular in South-Eastern Asia and therefore not a part of the FAME mixes designed for Europe) with shorter carbon chain lengths and therefore a lower molar mass, adding a concentration in mg/kg resulted in a greater quantity of carbonyl groups, and thus in a known systematic agreement. These deviations can easily and simply be corrected by a specific calibration. The currently approved methods can either not determine CME (GC-MS, GC-Heart Cut and HPLC), or have the same systematic agreement (FTIR Rapid Screening Method).

TABLE 2

FAME alone compared with FAME mix from B7 calibration

| Matrix | Analyte | Added concentration [mg/kg] | Calculated concentration [mg/kg] |
|---|---|---|---|
| Jet fuel | RME from B7 | 48.5 | 54.77 |
| Jet fuel | PME from B7 | 48.4 | 49.44 |
| Jet fuel | TME from B7 | 47.7 | 48.48 |
| Jet fuel | SME from B7 | 49.0 | 46.86 |
| Jet fuel | UCOME from B7 | 48.7 | 47.37 |
| Jet fuel | CME from B7 | 48.1 | 66.50 |

Additives:

At the maximum permitted concentration in jet fuel of 15 permitted additives of various types (Static Dissipator, Lubricity Improver, Fuel System Icing Inhibitor, Metal Deactivator, Antioxidant & Cetane Improver, Biocide), an error in the measured value of <±5 mg/kg was measured. This is within the limits of the expected reproducibility of the method.

Jet Fuel Screening:

The determination of FAME in 26 different jet fuels showed that throughout, deviations from the nominal value could arise (73%≤5 mg/kg, or 92%≤7.5 mg/kg). Such severe discrepancies are known from global jet fuel surveys from the British Energy Institute (n=189; 85%<5 mg/kg, or 95%<10 mg/kg, measured by means of a FTIR Rapid Screening Method) and can be attributed to the different compositions and thus to spectral differences in real jet fuels.

FAEE in Jet Fuel by Means of Aminolysis

Aminolysis also functions with Fatty Acid Ethyl Ester (FAEE), but compared with FAME, a different wave number has to be evaluated. Table 3 shows the results for a calibration with FAEE, in this case ethyl palmitate, in various concentrations, with a symmetrical evaluation about 1749 cm$^{-1}$.

TABLE 3

FAEE in jet fuel using aminolysis

| Matrix | Analyte | Added concentration [mg/kg] | Calculated concentration [mg/kg] |
|---|---|---|---|
| Jet fuel | FAEE | 0 | 0.89 |
| Jet fuel | FAEE | 50 | 48.66 |

TABLE 3-continued

FAEE in jet fuel using aminolysis

| Matrix | Analyte | Added concentration [mg/kg] | Calculated concentration [mg/kg] |
|---|---|---|---|
| Jet fuel | FAEE | 100 | 100.23 |
| Jet fuel | FAEE | 200 | 200.22 |

In samples which contained both FAEE and FAME, the choice of wave numbers for the evaluation meant that the two analytes could be determined independently of each other. Table 4 shows, by way of example, the determination of FAME from a sample which contained both FAME and FAEE.

TABLE 4

Determination of FAME in a mixture of FAME and FAEE

| Matrix | Analyte | Added concentration of FAME [mg/kg] | Added concentration of FAEE [mg/kg] | Calculated concentration of FAME [mg/kg] |
|---|---|---|---|---|
| Jet fuel | FAME & FAEE | 0 | 103.5 | −3.29 |
| Jet fuel | FAME & FAEE | 198.4 | 103.5 | 196.26 |

Glyceryl Trioleate in Jet Fuel Using Aminolysis

The aminolysis of triglycerides leads to the formation of amides and alcohol. This reaction was carried out with glyceryl trioleate in jet fuel with lipase as the catalyst. Table 5 shows the results for various concentrations.

TABLE 5

Triglyceride in jet fuel using aminolysis

| Matrix | Analyte | Added concentration [mg/kg] | Calculated concentration [mg/kg] |
|---|---|---|---|
| Jet fuel | Glyceryl trioleate | 0.0 | −0.98 |
| Jet fuel | Glyceryl trioleate | 5.0 | 3.14 |
| Jet fuel | Glyceryl trioleate | 19.9 | 20.18 |
| Jet fuel | Glyceryl trioleate | 49.8 | 48.65 |
| Jet fuel | Glyceryl trioleate | 98.5 | 99.61 |

FAME in Diesel Using Aminolysis

In order to show that the method in accordance with the invention can also be extended to other liquid fuels, traces of FAME in a diesel B0 matrix were measured. The results of the enzymatically catalysed aminolysis of FAME in diesel are listed in Table 6.

TABLE 6

FAME in diesel using aminolysis

| Matrix | Analyte | Added concentration [mg/kg] | Calculated concentration [mg/kg] |
|---|---|---|---|
| Diesel | FAME mix from B7 | 0.0 | −0.27 |
| Diesel | FAME mix from B7 | 10.0 | 10.27 |
| Diesel | FAME mix from B7 | 19.9 | 20.86 |
| Diesel | FAME mix from B7 | 49.2 | 50.19 |
| Diesel | FAME mix from B7 | 198.7 | 198.08 |

FAME in Jet Fuel by Transesterification

Figure 3:
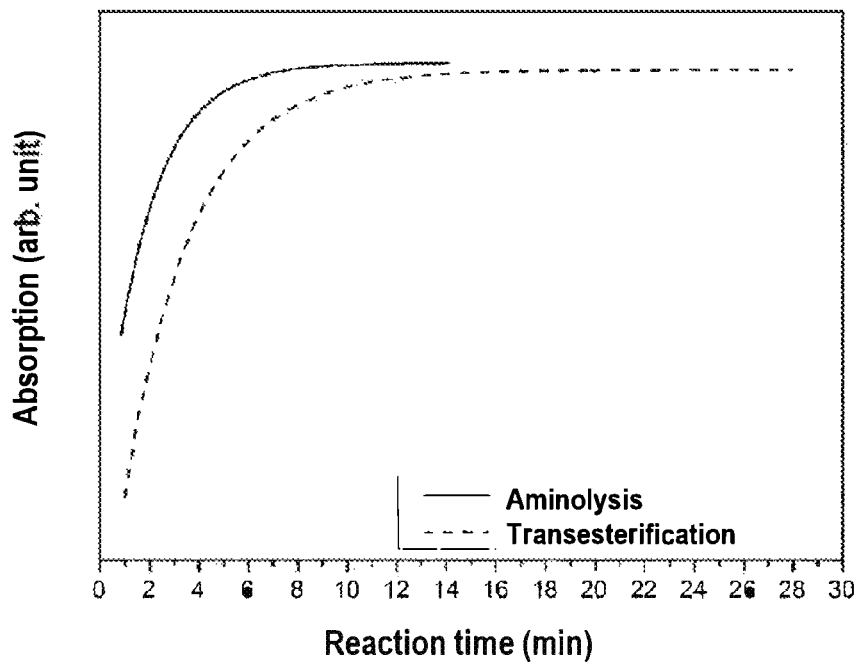
FIG. 3: shows the comparison of the reaction kinetics for transesterification and aminolysis.

The transesterification of FAME with alcohols results in the formation of other esters. Because of the small separation of the characteristic bands between the analyte and reaction product compared with aminolysis, in the case of transesterification, somewhat poorer values were obtained for the reproducibility of the method and the error in the measured values. It can be seen from the reaction kinetics shown in FIG. 3 that the transesterification took approximately ten minutes longer than the aminolysis. For these reasons, the catalytic-enzymatic aminolysis of FAME in jet fuel was established as the preferred implementation of the method.

Reaction of Fatty Acid Esters and Other Analytes

Figure 4:
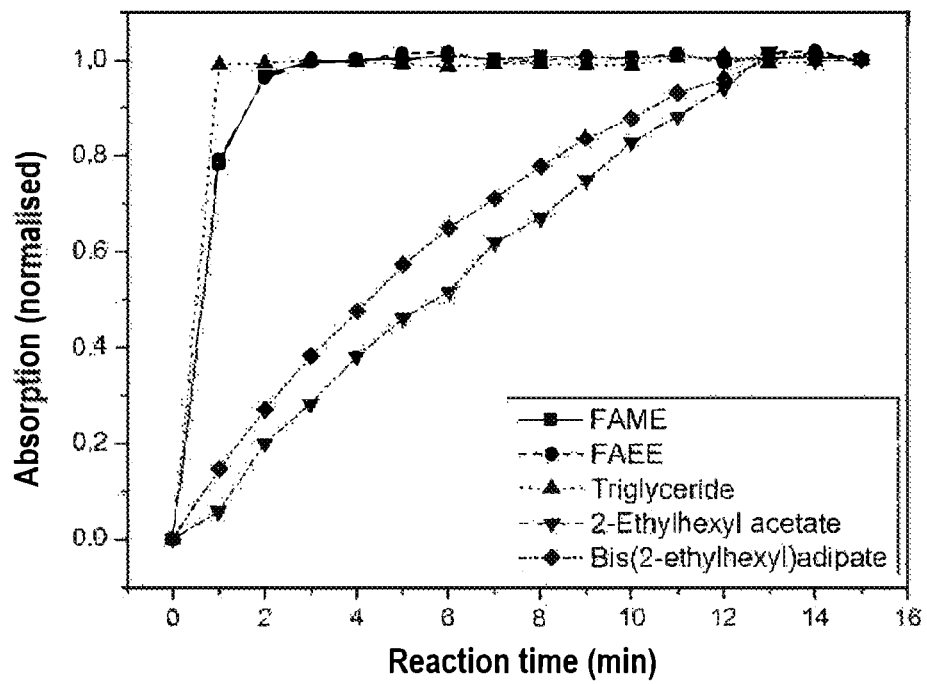
FIG. 4: shows the reactions of fatty acid esters and other analytes measured on a measurement system with FTIR in accordance with the method in accordance with the invention.

FIG. 4 shows the reactions of FAME, FAEE, triglycerides, diethylhexyl adipate and 2-ethylhexyl acetate, measured with a measurement system with FTIR in accordance with the method in accordance with the invention. The wave numbers for the evaluation in this regard were tailored to the respective analytes.

From the profile of the curves in FIG. 4, it can be seen that a qualitative prediction of the type of analyte can be made from the reaction kinetics of the analyte. As an example, compared with FAME, FAEE and triglycerides, the plasticizer diethylhexyl adipate and the interferent 2-ethylhexyl acetate have a significantly slower reaction rate. Consequently, FAME, FAEE and triglycerides can be distinguished from the other test analytes which, as interferents, could falsify FTIR measurements in accordance with the prior art and the quantitative determination of FAME, FAEE and triglycerides. By means of the combination of optimized evaluation wave numbers and the profile of the reaction kinetics for the analytes, other substances can be taken into consideration separately from each other. The method for the separate measurement and determination of contamination by fatty acid esters can also be applied to other substances.

What is claimed is:

1. A method for the quantitative determination of contaminants in the form of fatty acid esters in jet fuels, wherein the analyte is the fatty acid ester fatty acid methyl ester (FAME) and/or the fatty acid ester fatty acid ethyl ester (FAEE), wherein the analyte undergoes a chemical reaction which is selective for it and which influences the intensity for the carbonyl band of the respective ester group with the formation of a modified analyte and the variation in the concentration of analyte in the sample, which is the jet fuel together with FAME and/or FAEE, is measured using the reduction in the intensity of the carbonyl band and/or the increase in the concentration of the modified analyte is measured using the increase in the intensity of a band which is characteristic for the modification.

2. The method as claimed in claim 1, characterized in that the measurement of the variation in the concentration of analyte is carried out using IR spectroscopy.

3. The method as claimed in claim 2, characterized in that the measurement of the variation in the concentration of analyte is carried out using FTIR spectroscopy.

4. The method as claimed in claim 2, characterized in that the measurement of the variation in the concentration of analyte is carried out using quantum cascade lasers.

5. The method as claimed in claim 2, characterized in that the measurement of the variation in the concentration of analyte is carried out by means of IR spectroscopy with the aid of the reduction in the carbonyl band at 1749 $cm^{-1}$ or 1742 $cm^{-1}$.

6. The method as claimed in claim 5, characterized in that the measurement of the variation in the concentration of analyte is carried out by means of IR spectroscopy with the aid of the reduction in the carbonyl band at 1749 $cm^{-1}$ by symmetrical evaluation about 1742 $cm^{-1}$ or with the aid of the reduction in the carbonyl band at 1742 $cm^{-1}$ by symmetrical evaluation about 1749 $cm^{-1}$.

7. The method as claimed in claim 1, characterized in that FAME/FAEE is transformed into the corresponding amide by adding an amine, wherein the variation in the concentration of FAME/FAEE in the sample is measured-with the aid of the reduction in the intensity of the carbonyl band for the ester and/or the increase in the intensity of the amide band for the amide which is formed.

8. The method as claimed in claim 7, characterized in that the reaction is enzymatically catalysed.

9. The method as claimed in claim 1, characterized in that FAME/FAEE is transformed into the corresponding other ester by adding another alcohol under suitable reaction conditions and the variation in the concentration of FAME/FAEE in the sample is measured with the aid of the reduction in the intensity of the carbonyl band for the ester and/or the increase in the intensity of the carbonyl band of the other ester.

10. The method as claimed in claim 9, characterized in that the reaction is enzymatically catalysed.

11. The method as claimed in claim 1, characterized in that in addition to the quantitative determination, the method additionally comprises a qualitative determination using the reaction kinetics or reaction kinetics.

12. Use of a method as claimed in claim 1, characterized in that the method is used for identification of the contaminant or for the exclusion of the contaminant.

* * * * *